(12) United States Patent
Rivest et al.

(10) Patent No.: US 12,296,136 B2
(45) Date of Patent: May 13, 2025

(54) CORRUGATED MEDICAL TUBING SYSTEM HAVING FITTING WITH ANTI-TAMPER SLEEVE

(71) Applicant: Omega Flex, Inc., Middletown, CT (US)

(72) Inventors: Dean W. Rivest, Oxford, PA (US); David R. Elder, Liberty, PA (US); Andrew Moore, Coatesville, PA (US)

(73) Assignee: OMEGA FLEX, INC., Middletown, CT (US)

( * ) Notice: Subject to any disclaimer, the term of this patent is extended or adjusted under 35 U.S.C. 154(b) by 968 days.

(21) Appl. No.: 16/961,155

(22) PCT Filed: Jan. 8, 2019

(86) PCT No.: PCT/US2019/012635
§ 371 (c)(1),
(2) Date: Jul. 9, 2020

(87) PCT Pub. No.: WO2019/143497
PCT Pub. Date: Jul. 25, 2019

(65) Prior Publication Data
US 2020/0398038 A1    Dec. 24, 2020

Related U.S. Application Data

(60) Provisional application No. 62/619,186, filed on Jan. 19, 2018.

(51) Int. Cl.
*A61M 39/10* (2006.01)
*A61M 39/12* (2006.01)
*F16L 25/00* (2006.01)

(52) U.S. Cl.
CPC ........ *A61M 39/1011* (2013.01); *A61M 39/12* (2013.01); *F16L 25/0036* (2013.01);
(Continued)

(58) Field of Classification Search
CPC ..... F16L 25/0036; F16L 33/223; F16L 33/26; F16L 2201/20
See application file for complete search history.

(56) References Cited

U.S. PATENT DOCUMENTS 3,454,290 A    7/1969  Tairraz
4,286,640 A *  9/1981  Knox ................... A61J 1/1425
(Continued)

FOREIGN PATENT DOCUMENTS

CN    1440498 A    9/2003
CN    105020395 A   11/2015
(Continued)

OTHER PUBLICATIONS

Chinese Office Action for Application No. 201980007082.3; Issued Dec. 30, 2021; 8 Pages.
(Continued)

*Primary Examiner* — Zachary T Dragicevich
(74) *Attorney, Agent, or Firm* — CANTOR COLBURN LLP

(57) ABSTRACT

A fitting for use with metal, corrugated tubing having peaks and valleys includes a nut configured to receive the tubing; a sealing member for placement in a valley of the tubing, the sealing member including a sealing surface; an adaptor configured to engage the nut, the adaptor including an adaptor sealing surface; and an anti-tamper sleeve configured to encompass the nut and adaptor; wherein upon assembly, the tubing is compressed between the adaptor sealing surface and the sealing surface.

14 Claims, 3 Drawing Sheets

(52) U.S. Cl.
CPC ............... *A61M 2039/1033* (2013.01); *A61M 2039/1077* (2013.01)

(56) References Cited

U.S. PATENT DOCUMENTS

| | | | | |
|---|---|---|---|---|
| 4,340,052 | A | * | 7/1982 | Dennehey ........... A61M 39/1011 |
| 4,379,009 | A | * | 4/1983 | Shibata .................. F16L 23/00 |
| 4,674,775 | A | * | 6/1987 | Tajima ................ F16L 25/0036 |
| 5,531,695 | A | * | 7/1996 | Swisher ............. A61M 39/1011 |
| 6,428,052 | B1 | * | 8/2002 | Albino ................ F16L 25/0036 |
| 7,004,510 | B2 | | 2/2006 | Treichel |
| 2002/0117226 | A1 | * | 8/2002 | Malcarne, Jr. ...... F16L 25/0036 |
| 2005/0285401 | A1 | | 12/2005 | Treichel et al. |
| 2006/0061103 | A1 | | 3/2006 | Gronquist |
| 2010/0148501 | A1 | | 6/2010 | Bennett et al. |
| 2010/0209178 | A1 | * | 8/2010 | Oh ...................... F16L 25/0036 |
| 2011/0041944 | A1 | | 2/2011 | Duquette et al. |
| 2014/0036448 | A1 | | 2/2014 | Kim et al. |
| 2014/0306448 | A1 | | 10/2014 | Rivest |
| 2016/0123506 | A1 | | 5/2016 | Strunk |
| 2017/0072254 | A1 | | 3/2017 | Ryu et al. |
| 2018/0038533 | A1 | * | 2/2018 | Ibayashi ................. F16L 33/26 |
| 2018/0216762 | A1 | | 8/2018 | Rivest |
| 2019/0120411 | A1 | * | 4/2019 | Choi ....................... F16L 33/26 |

FOREIGN PATENT DOCUMENTS

| | | |
|---|---|---|
| CN | 205824411 U | 12/2016 |
| JP | S60184488 U | 12/1985 |
| JP | H04307193 A | 10/1992 |
| JP | 2007292281 A | 11/2007 |
| UA | 201005038 | 11/2011 |

OTHER PUBLICATIONS

Taiwan Office Action for Application No. 108101537; Issued Feb. 14, 2022; 8 Pages.
Japanese Office Action for Application No. 2020-539269; Issued Oct. 4, 2022; 7 Pages.
European Extended European Search Report for Application No. 19741175.4; Issued Sep. 16, 2021; 9 Pages.
International Search Report and Written Opinion for application PCT/US2019/12635, dated Apr. 15, 2019, 11 pages.
MediTrac.Us, "MediTrac" online Feb. 1, 2018, retrieved from internet Jan. 3, 2019, http://meditrac.us, entire document, 6 pages.
Vimeo.com , "Omegaflex Introducing Meditrac", online Jan. 15, 2018, retrieved Jan. 3, 2019 https://vimeo.com/251184693, entire document, 6 pages.
Japanese Office Action for Application No. 2020539269, Issued Sep. 14, 2023, 5 Pages.
Ukrainian Office Action for Application No. A202004807, Issued Aug. 18, 2023, 5 Pages.
Unknown, "Stainless Steel Corrugated Hose Exporters" Ambicaflex Technology, Oct. 15, 2015, 4 Pages. https://www.ambicaflex.com/stainless-steel-corrugated-hose.htm.
Israeli Office Action for Application No. 275885, Issued Mar. 6, 2025, 4 Pages.

* cited by examiner

CORRUGATED MEDICAL TUBING SYSTEM HAVING FITTING WITH ANTI-TAMPER SLEEVE

BACKGROUND

Medical piping within health care facilities was traditionally copper tubing meeting NPFA 99 health care facilities code. The health care facilities range from hospitals, ambulatory health care centers and clinics to medical and dental offices, nursing homes and limited care facilities. Rigid copper tubing can be difficult to install.

SUMMARY

Embodiments of the invention are directed to a fitting for use with corrugated medical tubing system that replaces traditional brazed copper tubing In an embodiment, a fitting for use with metal, corrugated tubing having peaks and valleys includes a nut configured to receive the tubing; a sealing member for placement in a valley of the tubing, the sealing member including a sealing surface; an adaptor configured to engage the nut, the adaptor including an adaptor sealing surface; and an anti-tamper sleeve configured to encompass the nut and adaptor; wherein upon assembly, the tubing is compressed between the adaptor sealing surface and the sealing surface.

In addition to one or more of the features described herein, or as an alternative, further embodiments may include wherein the tubing is compressed between the adaptor sealing surface and the sealing surface comprises a double flare of tubing.

In addition to one or more of the features described herein, or as an alternative, further embodiments may include wherein the adaptor sealing surface is curved.

In addition to one or more of the features described herein, or as an alternative, further embodiments may include wherein the adaptor includes adaptor engagement threads to engage nut engagement threads on the nut.

In addition to one or more of the features described herein, or as an alternative, further embodiments may include wherein the adaptor includes a retaining surface to provide an interference fit with the anti-tamper sleeve.

In addition to one or more of the features described herein, or as an alternative, further embodiments may include wherein the anti-tamper sleeve includes a first inner diameter and a second inner diameter, the first inner diameter less than the second inner diameter, the first inner diameter engaging the retaining surface of the adaptor.

In addition to one or more of the features described herein, or as an alternative, further embodiments may include a rear jacket lock sleeve and a jacket lock, the jacket lock configured to engage a jacket of the tubing.

In addition to one or more of the features described herein, or as an alternative, further embodiments may include wherein the jacket lock includes at least one jacket lock groove on an interior surface of the jacket lock.

In addition to one or more of the features described herein, or as an alternative, further embodiments may include wherein the jacket lock includes a jacket lock taper and the jacket lock sleeve includes a tapered surface configured to engage the jacket lock taper to compress the jacket lock and reduce a diameter of the jacket lock.

In another embodiment, a tubing system includes a fitting secured to a metal, corrugated tubing having peaks and valleys, the fitting including a nut positioned about the tubing; a sealing member located in a valley of the tubing, the sealing member including a sealing surface; an adaptor engaging the nut, the adaptor including an adaptor sealing surface; and an anti-tamper sleeve encompassing the nut and adaptor; wherein the tubing is compressed between the adaptor sealing surface and the sealing surface.

Technical effects of embodiments of the disclosure include the ability to provide a flexible piping solution along with a tamper-proof construction.

DETAILED DESCRIPTION

Figure 1:
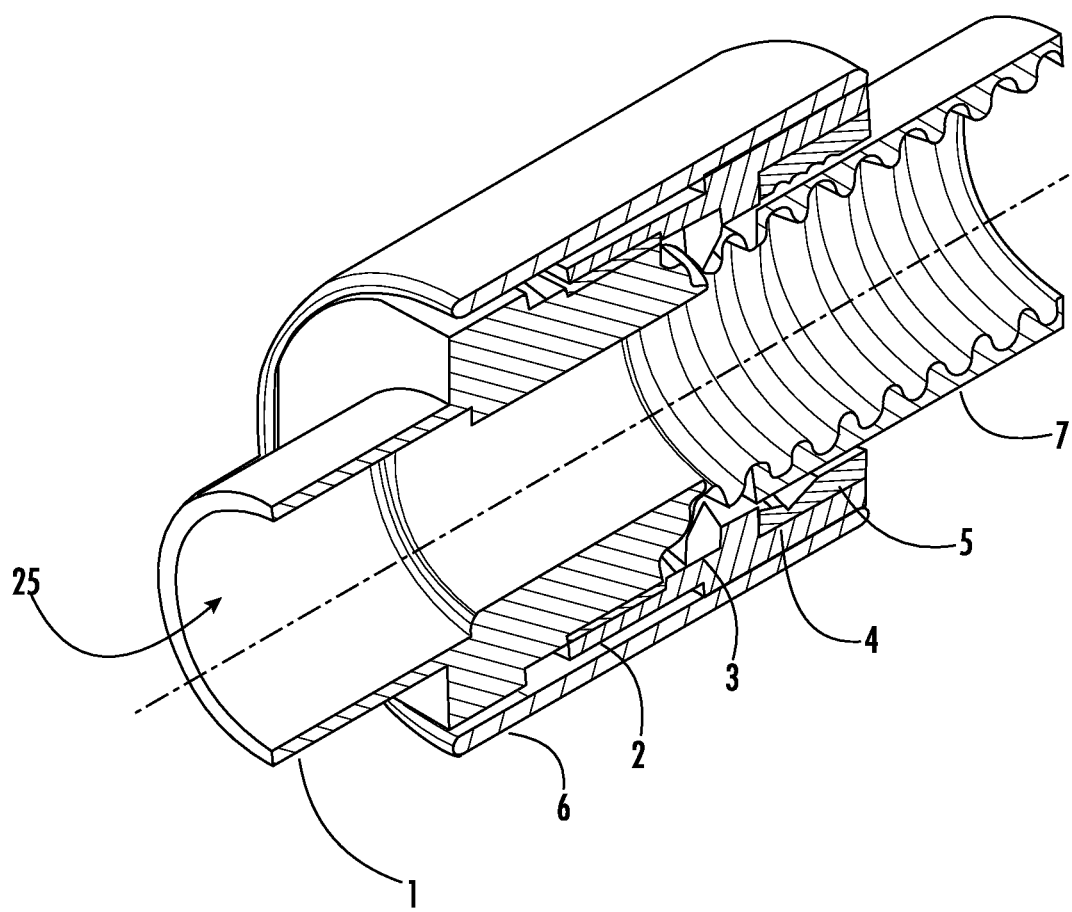
FIG. 1 is a perspective view of a fitting swaged onto corrugated medical tubing.
Figure 2:
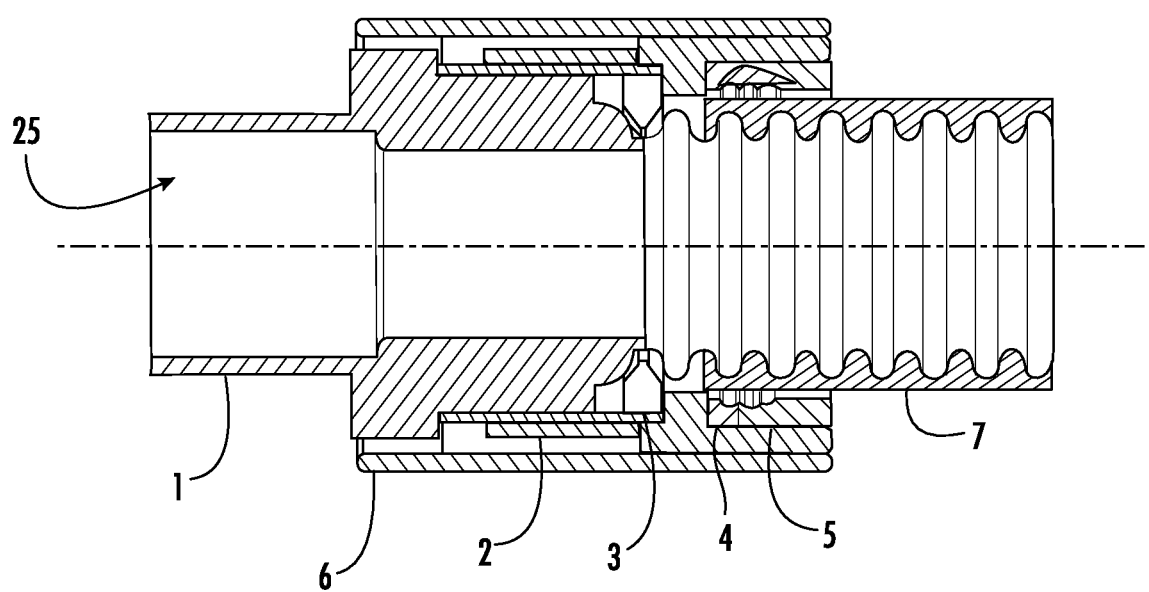
FIG. 2 is a cross-sectional view of a fitting swaged onto corrugated medical tubing.

Referring to FIGS. 1 and 2, a tubing system includes an end fitting axially swaged onto the end of corrugated medical tubing 7. The axially swaged fitting includes an adaptor 1, a sealing member 3, which may be in the form of a split ring set, an axially swaged nut 2, a jacket lock 4, a rear axially swaged jacket lock sleeve 5, and an anti-tamper sleeve 6, all manufactured, for example, from a metal such as brass or stainless steel. Existing rigid copper tubing is received in pocket 25 of adaptor 1 (FIG. 1) and secured to the adaptor 1, for example, by brazing. The sealing member 3 may be implemented using components other than a split ring set, such as a collet, etc. The corrugated medical tubing 7 includes corrugated primary tubing manufactured from, for example, a metal such as a copper alloy, or stainless steel, covered with a nonmetallic jacket which fills the spaces between the corrugations, thereby mechanically attaching the jacket to the corrugated primary tubing. The jacket may be coextruded with the tubing.

The adaptor 1 engages the corrugated medical tubing 7, and creates a double-flare of metal with one end corrugation, there by creating a primary seal. The end corrugation is supported by the sealing member 3, which incorporates a tapered sealing surface, which may be about 35°. The sealing member 3 is located in the last full corrugation of the tubing 7 and is held in place by the axially swaged nut 2. The axially swaged nut 2 is threaded onto the adaptor 1. The adaptor 1 sealing surface may be non-linear, such as curved or spherical. The motion of capturing the sealing member 3 and threading the axially swaged nut 2 over the adaptor sealing surface creates the compressive load necessary to create the metal-to-metal primary seal between the adaptor 1 and the corrugated medical tubing 7.

The rear jacket lock sleeve 5 is axially swaged into the nut 2, and slides over the jacket lock 4 reducing the inside diameter of the jacket lock 4 thereby creating a radially compressive load between the jacket lock 4 and the jacket of the corrugated medical tubing 7. The jacket lock 4 contains a split to easily allow reduction of diameter. This mechanically attaches the fitting to the piping, preventing any expansion under pressure, and prevents the nut 2 from being removed.

The anti-tamper sleeve 6 is axially swaged over the nut 2 and adaptor 1. The anti-tamper sleeve is smooth on the exterior, the interference fit between the anti-tamper sleeve 6 and the adaptor 1 is great enough to prevent dis-assembly, thereby creating a permanently attached fitting. The anti-tamper sleeve 6 may be made from a metal, such as brass.

Figure 3:
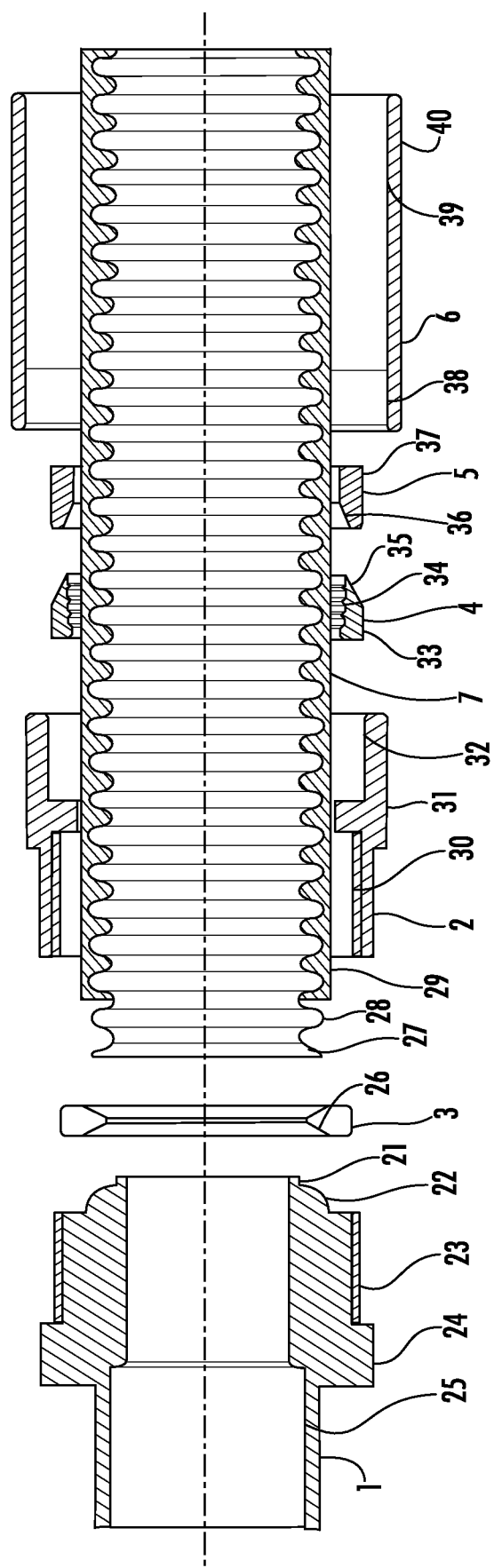
FIG. 3 is an exploded, cross-section view of a fitting and corrugated medical tubing.

Referring to FIG. 3, features of the tubing system are presented with numerals. A guiding diameter 21 on the adaptor 1 provides for centering an inner diameter of the corrugated medical tubing on to adaptor 1.

An adaptor sealing surface 22, mates with a double flare of corrugated medical tubing 7, which is supported by tapered sealing surface 26 (e.g., about 35 degrees) on sealing member 3. A curved or spherical adaptor sealing surface 22 provides a single line of contact with corrugated medical tubing 7, thereby reducing the compression axially load required to create a seal.

Adaptor engagement threads 23 on adaptor 1 engage nut engagement threads 30 on axially engaged nut 2.

A primary retaining surface 24 of the adaptor 1 provides an interference fit with the anti-tamper sleeve 6. A first inner diameter 38 of anti-tamper sleeve 6 is smaller than the diameter of surface 24, for example, by about 0.010 inches. This creates a strong interference between the anti-tamper sleeve 6 and adaptor 1 to defeat rotation of the anti-tamper sleeve.

A pocket 25 provides for attaching to copper tubing, such as by brazing.

Sealing surface 26 on sealing member 3 is tapered, to about 35 degrees. The sealing surface 26 provides rigidity to create a seal between the adaptor 1 and the axially swaged nut 2.

A double-flare 27 of metal is formed from a peak of the corrugated medical tubing 7. The double flare 27 is formed between the adaptor sealing surface 22 on adaptor 1 and sealing surface 26 on sealing member 3 when nut 2 is threaded onto adaptor 1.

The corrugated tubing profile 28, manufactured from copper alloy in an example embodiment, but could also be manufactured from stainless steel. Corrugations are annular in design.

A nonmetallic jacket 29 fills the spaces in between the corrugations of the corrugated medical tubing 7. Jacket 29 and has a smooth exterior. In an example embodiment, jacket 29 is manufactured from low density polyethylene, but other materials that offer sufficient tensile strength to resist corrugation movement under pressure could be utilized. Jacket 29 may meet ASTM E84, with maximum Flame Spread index of 25 and maximum Smoke Density Index of 50. Jacket 29 may be coextruded with metal tubing 28.

Nut 2 includes an anti tamper sleeve diameter 31 slightly smaller in diameter than a second inner diameter 39 of anti-tamper sleeve 6, for example, by about 0.005 inches.

A rear retaining diameter 32 of the axially swaged nut 2 mates with outer diameter 37 of the rear jacket lock sleeve 5. The jacket lock 4 has an outer diameter 33 which is slightly smaller than inner diameter 32 of the axially swaged nut 2. Jacket lock grooves 34 are formed on the interior surface of the jacket lock 4. One or more jacket lock grooves 34 compress and engage outside diameter of coextruded jacket 29.

Jacket lock 4 includes a jacket lock taper 35. The jacket lock taper 35 provides a centering and guiding mechanism to reduce the diameter of the jacket lock 4 when the rear jacket lock sleeve 5 is pressed over the jacket lock 4. The rear jacket lock sleeve 5 includes a tapered surface 36 that engages the jacket lock taper 35 to compress the jacket lock 4 and reduced the diameter of the jacket lock 4.

The rear jacket lock sleeve 5 has an outside diameter 37 that is slightly smaller than inner diameter 32 on axially swaged nut 2, thereby being forced into diameter 32 and mechanically fixing rear jacket lock sleeve 5 in place in the nut 2.

The anti-tamper sleeve 6 includes a first inner diameter 38 that is smaller in diameter than primary retaining surface 24 of the adaptor 1, for example by about 0.010 inches. The interference between the first inner diameter 38 of the anti-tamper sleeve 6 and the primary retaining surface 24 of the adaptor 1 provides a permanent attachment, and prevents the axially swaged nut 2 from being removed from the adaptor 1.

The anti-tamper sleeve 6 includes a second inner diameter 39 that is slightly larger in diameter than anti-tamper sleeve diameter 31 on axially swaged nut 2, for example by about 0.005 inches. This allows the anti-tamper sleeve 6 to slide over the nut 2. The anti-tamper sleeve 6 is forced onto the adaptor 1 via an interference fit between diameters 24 and 38. The first inner diameter 38 is smaller than the second inner diameter 39.

The anti-tamper sleeve 6 includes a smooth outside surface 40 that prevents disassembly of fitting. In assembly, the sealing member 3 is placed in a valley of the tubing 7. The nut 2 is threaded onto adaptor 1 to create the double flare of metal tubing seal. The jacket lock 4 and rear jacket lock sleeve 5 are pressed into inner diameter 32 of nut 2. The anti-tamper sleeve 6 may be press-fit over the adaptor 1 and nut 2 (e.g., moving from the adaptor 1 to the nut 2).

The term "about" is intended to include the degree of error associated with measurement of the particular quantity and/or manufacturing tolerances based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising." when used in this specification, specify the presence of stated features, integers, steps, operations, elements, and/or components, but do not preclude the presence or addition of one or more other features, integers, steps, operations, element components, and/or groups thereof.

Those of skill in the art will appreciate that various example embodiments are shown and described herein, each having certain features in the particular embodiments, but the present disclosure is not thus limited. Rather, the present disclosure can be modified to incorporate any number of variations, alterations, substitutions, combinations, sub-combinations, or equivalent arrangements not heretofore described, but which are commensurate with the scope of the present disclosure. Additionally, while various embodiments of the present disclosure have been described, it is to be understood that aspects of the present disclosure may include only some of the described embodiments. Accordingly, the present disclosure is not to be seen as limited by the foregoing description, but is only limited by the scope of the appended claims.

What is claimed is:

1. A fitting for use with metal, corrugated medical tubing having peaks and valleys, the fitting comprising:
a nut configured to receive the tubing;
a sealing member for placement in a valley of the tubing, the sealing member including a sealing surface;
an adaptor configured to engage the nut, the adaptor including an adaptor sealing surface; and an anti-tamper sleeve configured to encompass the nut and adaptor;
wherein upon assembly, the tubing is compressed between the adaptor sealing surface and the sealing surface of the sealing member;
wherein the anti-tamper sleeve is press-fit over the adaptor and nut via an interference fit between a retaining surface of the adaptor and an inner diameter of the anti-tamper sleeve.

2. The fitting of claim 1, wherein the compressed tubing comprises a double flare of tubing.

3. The fitting of claim 1 wherein the adaptor sealing surface is curved.

4. The fitting of claim 1 wherein the adaptor includes adaptor engagement threads to engage nut engagement threads on the nut.

5. The fitting of claim 1 wherein the anti-tamper sleeve includes a first inner diameter and a second inner diameter, the first inner diameter is less than the second inner diameter, the first inner diameter engaging the retaining surface of the adaptor.

6. The fitting of claim 1 further comprising a rear jacket lock sleeve and a jacket lock, the jacket lock configured to engage a jacket of the tubing.

7. The fitting of claim 1 wherein the interference fit between the retaining surface of the adaptor and the inner diameter of the anti-tamper sleeve is created by an inner diameter of the anti-tamper sleeve being smaller than a diameter of the retaining surface of the adaptor.

8. The fitting of claim 1 wherein the anti-tamper sleeve has a single, cylindrical outer surface.

9. The fitting of claim 1 wherein the interference fit between the retaining surface of the adaptor and the inner diameter of the anti-tamper sleeve is a radial interference fit.

10. The fitting of claim 1 wherein retaining surface of the adaptor corresponds to a largest outer diameter of the adaptor.

11. A fitting for use with metal, corrugated tubing having peaks and valleys, the fitting comprising:
a nut configured to receive the tubing;
a sealing member for placement in a valley of the tubing, the sealing member including a sealing surface;
an adaptor configured to engage the nut, the adaptor including an adaptor sealing surface;
an anti-tamper sleeve configured to encompass the nut and adaptor; and
a rear jacket lock sleeve and a jacket lock, the jacket lock configured to engage a jacket of the tubing;
wherein the jacket lock includes at least one jacket lock groove on an interior surface of the jacket lock.

12. A fitting for use with metal, corrugated tubing having peaks and valleys, the fitting comprising:
a nut configured to receive the tubing;
a sealing member for placement in a valley of the tubing, the sealing member including a sealing surface;
an adaptor configured to engage the nut, the adaptor including an adaptor sealing surface;
an anti-tamper sleeve configured to encompass the nut and adaptor; and
a rear jacket lock sleeve and a jacket lock, the jacket lock configured to engage a jacket of the tubing;
wherein the jacket lock includes a jacket lock surface and the jacket lock sleeve includes a tapered surface configured to engage the jacket lock surface to compress the jacket lock and reduce a diameter of the jacket lock.

13. A tubing system comprising:
metal, corrugated, medical tubing having peaks and valleys:
a fitting secured to the tubing, the fitting comprising:
a nut positioned about the tubing;
a sealing member located in a valley of the tubing, the sealing member including a sealing surface;
an adaptor engaging the nut, the adaptor including an adaptor sealing surface; and
an anti-tamper sleeve encompassing the nut and adaptor;
wherein the tubing is compressed between the adaptor sealing surface and the sealing surface of the sealing member;
wherein the anti-tamper sleeve is press-fit over the adaptor and nut via an interference fit between a retaining surface of the adaptor and an inner diameter of the anti-tamper sleeve.

14. A method for securing a fitting to metal, corrugated medical tubing having peaks and valleys, the method comprising:
obtaining a nut configured to receive the tubing;
obtaining a sealing member for placement in a valley of the tubing, the sealing member including a sealing surface;
obtaining an adaptor configured to engage the nut, the adaptor including an adaptor sealing surface; and
obtaining an anti-tamper sleeve configured to encompass the nut and adaptor;
obtaining a rear jacket lock sleeve and a jacket lock, the jacket lock configured to engage a jacket of the tubing;
wherein the jacket lock includes a jacket lock surface and the jacket lock sleeve includes a tapered surface configured to engage the jacket lock surface to compress the jacket lock and reduce a diameter of the jacket lock;
placing the sealing member in a valley of the tubing;
mating the adaptor and nut to compress the metal tubing between the adaptor sealing surface and the sealing surface;
press-fitting the anti-tamper sleeve over the adaptor and nut via an interference fit between a retaining surface of the adaptor and an inner diameter of the anti-tamper sleeve.

* * * * *